US008112150B2

(12) United States Patent
Naqvi et al.

(10) Patent No.: US 8,112,150 B2
(45) Date of Patent: Feb. 7, 2012

(54) OPTIMIZATION OF PACEMAKER SETTINGS

(75) Inventors: Tasneem Zehra Naqvi, Los Angeles, CA (US); Dean Carl Winter, Helotes, TX (US)

(73) Assignee: AtCor Medical Pty Ltd, West Ryde, New South Wales (AU)

( * ) Notice: Subject to any disclaimer, the term of this patent is extended or adjusted under 35 U.S.C. 154(b) by 298 days.

(21) Appl. No.: 12/397,891

(22) Filed: Mar. 4, 2009

(65) Prior Publication Data
US 2010/0228311 A1  Sep. 9, 2010

(51) Int. Cl.
*A61N 1/365* (2006.01)
(52) U.S. Cl. .......................................... 607/5
(58) Field of Classification Search .............. 607/4–5
See application file for complete search history.

(56) References Cited

U.S. PATENT DOCUMENTS

| | | | |
|---|---|---|---|
| 4,094,308 A * | 6/1978 | Cormier ................... | 600/528 |
| 5,088,491 A | 2/1992 | Schaldach | |
| 5,265,011 A * | 11/1993 | O'Rourke .................. | 600/485 |
| 5,392,780 A | 2/1995 | Ogino et al. | |
| 5,487,752 A | 1/1996 | Salo et al. | |
| 6,247,474 B1 | 6/2001 | Greeninger et al. | |
| 6,334,849 B1 * | 1/2002 | Sunagawa ................ | 600/485 |
| 6,792,308 B2 * | 9/2004 | Corbucci .................. | 607/17 |
| 2003/0065365 A1 | 4/2003 | Zhu et al. | |
| 2005/0027323 A1 | 2/2005 | Mulligan et al. | |
| 2006/0068452 A1 | 3/2006 | Goldknopf et al. | |
| 2006/0115856 A1 | 6/2006 | Goldknopf et al. | |
| 2006/0115867 A1 | 6/2006 | Goldknopf et al. | |
| 2006/0155202 A1 | 7/2006 | Arand et al. | |
| 2006/0278532 A1 | 12/2006 | Goldknopf et al. | |
| 2007/0017809 A1 | 1/2007 | Goldknopf et al. | |
| 2007/0042429 A1 | 2/2007 | Goldknopf et al. | |
| 2008/0195164 A1 | 8/2008 | Arand et al. | |
| 2008/0195168 A1 | 8/2008 | Arand et al. | |
| 2008/0289964 A1 | 11/2008 | Goldknopf et al. | |
| 2009/0061457 A1 | 3/2009 | Goldknopf et al. | |

FOREIGN PATENT DOCUMENTS

| | | |
|---|---|---|
| EP | 1055395 | 11/2000 |
| GB | 2089999 | 6/1982 |

OTHER PUBLICATIONS

SphygmoCor at the Heart of Cardiovascular Management, Operator's Manual, Atcor Medical, Copyright 2006, pp. 1-55.
Rafique AM and Naqvi TZ, "Novel Method for Biventricular Pacemaker Optimization by a Radial Artery Tonometer. The case report." Minerva Cardioangiol. Jun. 2007 55(3): 385-9 (best copy available).
Naqvi TZ, Rafique AM, "Echocardiography-guided pacemaker optimization and radial artery tonometry". J Card Failure 14(7):583-589, 2008.

\* cited by examiner

*Primary Examiner* — Scott Getzow
*Assistant Examiner* — Amanda Patton
(74) *Attorney, Agent, or Firm* — Andrus, Sceales, Starke & Sawall, LLP (57) ABSTRACT

The system provides information to facilitate efficient optimization of programmer settings for cardiac pacemakers. It uses simultaneous measurement of a patient's electrocardiogram and peripheral blood pressure waveform in order to calculate, in real-time, a value correlated to the patient's pre-ejection time (PET) and, optionally, ejection duration (ED) for the patient's left ventricle. The peripheral blood pressure waveform is preferably monitored with a wrist mounted tonometer. Data including the electrocardiogram and peripheral blood pressure trace, as well as the surrogate pre-ejection time interval (SPET) for each heart beat and trending is displayed on a computer monitor, thereby allowing a physician or nurse to quickly optimize PET for the patient and adjusting programmer settings for an implanted pacemaker.

22 Claims, 5 Drawing Sheets

OPTIMIZATION OF PACEMAKER SETTINGS

FIELD OF THE INVENTION

The invention relates to the optimization of programmable settings for cardiac pacemakers. In particular, it uses simultaneous measurement of a patient's electrocardiogram (ECG) and peripheral blood pressure waveform in order to calculate, in real-time, a value correlated to the pre-ejection time (PET) for the patient's left ventricle, thereby allowing a physician or nurse to quickly optimize PET for the patient when adjusting programmable settings for an implanted pacemaker. The system is also able to determine ejection duration (ED) for the patient's left ventricle.

BACKGROUND

A biventricular pacemaker is a type of cardiac pacemaker that can pace both the right and the left ventricle (typically the lateral wall of the left ventricle). By pacing both right and left ventricles, the pacemaker is able to resynchronize a heart whose opposing walls and right and left ventricles do not contract in synchrony. Biventricular pacemakers have at least two leads, one in the right ventricle to stimulate the septum, and the other inserted through the coronary sinus to pace the lateral wall of the left ventricle. There is typically also a lead in the right atrium to facilitate synchrony with atria contraction. The use of a biventricular pacemaker is generally referred to as cardiac resynchronization therapy (CRT).

Programmable biventricular pacemakers enable optimization of the various time delays between pacemaker timing pulses. This optimization procedure requires the physician or nurse to set delays between the various timing pulses. Its general purpose is to coordinate contraction of the various chambers in the heart to improve overall efficiency and function. This particularly holds true for atrioventricular (A-V) pacing delays whereby the time interval between paced or native atrial contraction can be timed with paced ventricular beat for best cardiac efficiency. Although it is generally believed that both ventricles should contract simultaneously for optimum cardiac performance, a V-V pacing delay is often also required to obtain coordinated contraction.

Most commercial pacemakers are externally programmable via a wireless communication system in which a wand is held near the patient's chest in order to facilitate communications with the implanted pacemaker. Wireless programming allows a physician to adjust the pacing mode for the individual patient, thereby generally providing some control over the filling and/or contraction of the heart both at the time of the initial implant and also on a recurring basis. Unfortunately, procedures used today to optimize pacemaker settings tend to be time-consuming and expensive. Thus, it is believed that many programmable pacemakers are implanted and put into use using default factory settings without optimizing the settings for the individual patient.

The most common method of optimization is echocardiographic-guided CRT optimization (echo-guided CRT optimization). While echo-guided CRT optimization may lead to improvement in cardiac function, it is laborious, expensive and generally inconvenient for the patient. In echo-guided CRT optimization, the patient's heart is ultrasonically imaged and measurements taken from the echocardiogram are used by the physician to adjust pacemaker settings. Such a procedure normally takes two to three hours for both the patient and the physician. Echo-guided optimization has been shown to provide incremental improvement in cardiac function and patient functional class. However, in routine clinical practice the procedure may be incorrectly performed due to time constraints or lack of understanding of cardiac hemodynamics by the operator as well the methodological variability of echocardiographic measurements. This can, in turn, worsen patient symptoms. Hence, routine application of echo-guided CRT optimization is limited.

Efforts have been made in the art to assess the patient's cardiac function during pacemaker optimization without the need for subjecting the patient and the physician to an echocardiogram session. For example, it is known in the art to simultaneously sense ECG electrical and heart sound acoustic signals and process and display such data in order to assist CRT optimization without the need for echocardiography. See, for example, pending U.S. Application Publication No. 2006/0155202 A1, published on Jul. 13, 2006 to Arand et al., which is entitled "Hemodynamic Assessment/Adjustment"; Publication No. US2008/0195168 A1, published on Aug. 14, 2008 to Arand et al., which is entitled "Pacemaker-Patient Hemodynamic Assessment/Adjustment System"; and Publication No. US2008/0195164 A1, published on Aug. 14, 2008 to Arand et al., which is entitled "Pacemaker-Patient Hemodynamic Assessment/Adjustment Methodology".

The systems described in the above published patent applications use disposable microphones mounted to the patient's chest to produce a phonogram which plots detected heart sound over time. This system generally monitors the function of the left ventricle by comparing the onset of the QRS complex in the patient's electrocardiogram to the sonically detected closure of the mitral valve (the valve that lies between the left atrium and the left ventricle) and to the sonically detected closure of the aortic valve (the valve from the left ventricle to the aorta). These patent applications define the time between the onset of the QRS complex in the electrocardiogram and the closure of the mitral valve as the electromechanical activation time, which is also sometimes referred to in the art as electromechanical delay (EMD). These patent applications explain that a shortened electromechanical activation time generally correlates with improved heart function. These patents also define the time interval between the closure of the mitral valve and the closure of the aortic valve as the left ventricular systolic time, and explain that a lengthened left ventricle systolic time generally correlates with improved heart function as well. The system is also capable of measuring some other parameters as well such as intensity abnormal of heart sounds that correlate with worse cardiac function.

Prior work of one of the inventors of the present invention has involved the use of radial artery tonometry and biventricular pacemaker optimization. The results of some of this work are published in Rafique A M and Naqvi T Z, "Novel Method For Biventricular Pacemaker Optimization By A Radial Artery Tonometer. the case report." Minerva Cardioangiol. June 2007, 55(3): 385-9 and the use of this device in a series of 60 patients in Naqvi T Z, Rafique A M: Echocardiography-guided pacemaker optimization and radial artery tonometry. *J Card Failure* 14(7):583-589, 2008. In particular, this work involves the analysis of the patient's radial pressure waveform to determine the length of time between the opening and closing of the aortic valve, which is often referred to in the art as ejection duration (ED). Generally speaking, an optimum ejection duration is about 300 milliseconds in a healthy patient. A lowered ED value can indicate systolic failure. In a healthy subject, a heightened ED value may indicate diastolic failure, whereas in a patient with heart failure, increase in ED in particular to changes in pacemaker timings indicates improvement in heart's pumping function and hence its duration as measured by ED.

The assignee of the present application, AtCor Medical, manufactures the SphygmoCor® system which is able to non-invasively collect peripheral blood pressure pulse waveform data as well as ECG data. The commercial SphygmoCor® system includes a hand-held tonometer that is normally held against the patient's wrist by a pen like device or a wrist band, in order to collect pressure waveform data from the patient's radial artery. The signal from the tonometer as well as the signals from the ECG electrodes are transmitted to a digital signal processing module, and data is then transmitted from the module to a PC which is programmed with data acquisition and analysis software. The commercial SphygmoCor® system is able to determine the ejection duration (ED) from peripheral waveform data via algorithms that detect the onset of the systolic pressure waveform (i.e. corresponding to the opening of the aortic valve) and the incisura in the peripheral pulse waveform (i.e. corresponding to the closure of the aortic valve). The current SphygmoCor® system generally uses the ECG signals to analyze pulse wave velocity and heart rate variability.

During CRT optimization, physicians try to coordinate cardiac muscle contraction in order to minimize the isovolumetric contraction time (IVCT) and increase the ED in the left ventricle. The isovolumetric contraction time interval begins when the mitral valve closes, and ends when the blood pressure within the left ventricle is sufficient to open the aortic valve. The time from the onset of electrical cardiac activity (as marked by the onset of Q-wave of the ECG) and the closure of the mitral valve is termed the electrical mechanical delay (EMD). The combination of EMD and IVCT is referred to in the art as the pre-ejection time (PET) interval, and is a particularly useful parameter for CRT optimization. As mentioned, echo-guided CRT optimization is time-consuming and rather expensive. Also, non-invasive heart sound acoustic monitors are not well suited to detect the opening of the aortic valve and are therefore not well suited to measure either PET or IVCT. In addition, the surrogate of ED called LV systolic time (LVST) as measured by time interval between closure of mitral and aortic valves incorporates IVCT in its measurement. This makes measurement of LVST less reliable than ED as measured by SphygmoCor® system.

The primary purpose of the invention is to provide a convenient, non-invasive means for monitoring the pre-injection time (PET) and ejection duration (ED) of the systolic phase of the heart cycle, thereby enabling medical staff to efficiently optimize programmable settings for an implanted biventricular pacemaker.

SUMMARY OF THE INVENTION

The invention is a method and a system that conveniently and non-invasively monitors parameters pertaining to the pre-ejection time (PET) interval for a patient's left ventricle. The invention allows attending medical staff to quickly optimize PET for cardiac pacemaker patients when conducting cardiac resynchronization therapy (CRT) optimization. It also optionally measures the ejection duration (ED) for the patient's left ventricle, as is known in the art, which is also a helpful parameter for CRT optimization.

In one aspect, the invention is a method in which the electrical activity of a patient's heart is measured using a conventional electrocardiogram (ECG) technique. Simultaneously, the patient's peripheral pressure waveform is measured. Preferably, a tonometer mounted in a fixed position on the patient's wrist, for example using a wrist strap, is used to measure the pressure waveform of the patient's radial artery.

For each respective pulse, the electrocardiogram for each respective pulse, the electrocardiogram is analyzed to determine a time correlating to the ventricular impulse and this time is defined as an impulse time ($T_0$) for the contracting ventricle, e.g. the time at which the Q-wave reaches a minimum value or alternatively the time corresponding to the onset of the QRS complex. In accordance with the invention, the time ($T_2$) corresponding to the realization of systolic onset in the detected peripheral pressure waveform is also determined for each respective pulse. In the preferred embodiment of the invention, time $T_2$ corresponding to the onset of systole in the measured peripheral pressure waveform is determined by analyzing the first derivative of the peripheral pressure waveform and identifying a first negative to positive zero crossing preceding a maximum value for the first derivative. In accordance with the invention, the time values $T_0$ and $T_2$ are used to calculate a surrogate pre-ejection time interval (SPET) for the pulse. This information (SPET) and trends of this information, can be used conveniently by a medical staff in order to optimize CRT adjustments.

As mentioned, the pre-ejection time (PET) interval is a combination of electromechanical delay (EMD) plus isovolumetric contraction time (IVCT). IVCT is the time in the initial stages of ventricular contraction from when the mitral valve closes to when the aortic valve opens. The opening of the aortic valve is marked by the abrupt rise of pressure in the aorta, which results in a pressure pulse waveform rising to a peak systolic pressure and then declining. The time ($T_1$) marks the opening of the aortic valve. The time ($T_2$) marks the arrival of the foot of the pressure wave at the peripheral artery, e.g. a radial artery. The transit time (K) for the pressure wave to travel to the peripheral (e.g., radial) artery is the difference $T_2-T_1$. For any individual patient, the travel distance for a pressure wave from the aorta to a peripheral location remains constant when the patient is at rest during a CRT optimization session, as long as the peripheral pressure is measured at a fixed location (e.g., at a fixed location on the user's wrist to measure the pressure waveform at the radial artery). In accordance with the invention, it is assumed that the pulse wave velocity for the patient remains constant over the timeframe required for CRT optimization as long as the patient remains at rest. Testing indicates that this assumption is quite accurate. Thus, the time interval between the Q-wave ($T_0$) in an electrocardiogram and the foot ($T_2$) of the peripheral pressure wave, when the ECG and radial waveform are measured simultaneously, represents the pre-ejection time (PET) interval plus a fixed value (K), which combined is herein described as a surrogate pre-ejection time (SPET). Assuming that the minimum value of PET corresponds to the optimal settings for the pacemaker programming device, the constant offset (K) between the actual PET and the surrogate SPET does not affect the identification of settings corresponding to a minimum PET value.

In another aspect, the invention pertains to a system which includes hardware components and software tools that are particularly well suited to conveniently assist medical staff during CRT optimization by providing information relating to the patient's surrogate pre-ejection time (SPET). The preferred system uses much of the same hardware that is currently available in a SphygmoCor® system, utilizing an MM3™ digital signal processing electronic module. The leads from ECG electrodes are connected to the electronics module as is the cable from a blood pressure sensor, such as a tonometer. The preferred tonometer, as mentioned above, is strapped to the patient's wrist in a fixed location while the attending staff conducts CRT optimization. Analog data is sent from the electronics module to an A/D converter and the resulting digital data is analyzed and displayed via a programmed personal computer. Software on the personal computer preferably displays traces of the electrocardiogram data and the peripheral pressure waveform data as a function of time, and in real-time. The software allows the attending staff to select a given series of data representing a series of heart beats for which the surrogate pre-ejection time (SPET) is calculated for each pulse. The system preferably displays the data for each heart beat as well as an average and standard deviation for the selected series of heart beats. The system also allows the user to store data for later analysis. Typically, attending staff would adjust settings for the programmable pacemaker during CRT optimization, and compare SPET data from a previous setting to the current setting in an attempt to optimize (e.g. minimize) SPET. If desired, the system can also calculate and display other additional parameters as well. For example, as an optional feature, the system determines and displays ejection duration (ED) calculated from the peripheral pressure waveform, as is known in the art.

Further objects, features and advantages of the invention will be apparent from the following drawings and detailed description thereof.

BRIEF DESCRIPTION OF THE DRAWINGS

FIG. 4 is a graphical screen display similar to that shown in FIG. 3, however, FIG. 3 is intended to represent an example of data displayed prior to CRT optimization, whereas FIG. 4 is intended to represent data displayed after CRT optimization.

DETAILED DESCRIPTION OF THE DRAWINGS

Figure 1:
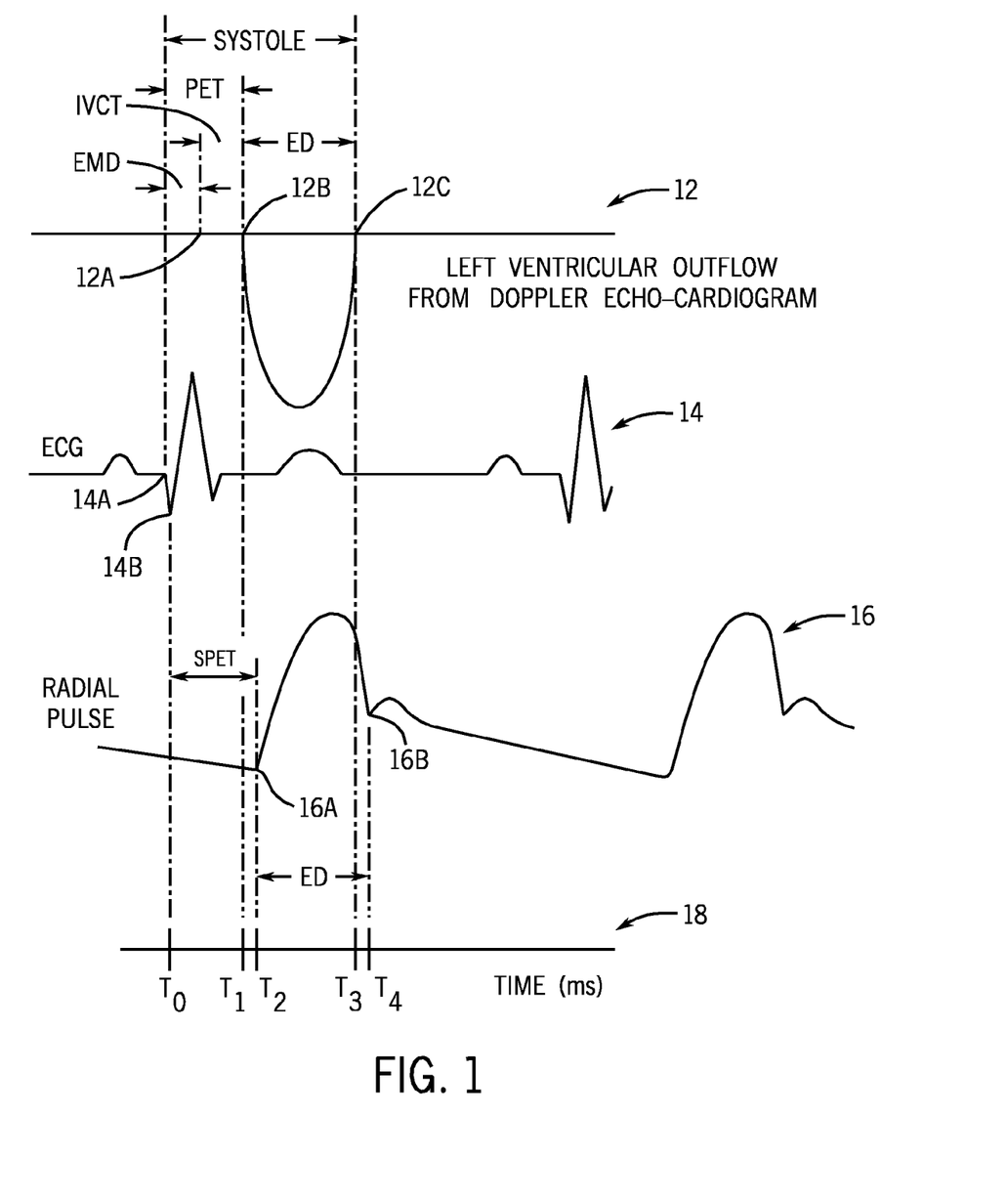
FIG. 1 is a schematic diagram illustrating blood flow through a patient's left ventricle as well as a corresponding typical electrocardiogram, and radial artery pressure pulse waves.

FIG. 1 illustrates a schematic plot 10 with a variety of illustrative data relating to an illustrative patient's cardiac cycle. In FIG. 1, curve 12 illustrates the outflow of blood from the patient's left ventricle as a function of time measured via a Doppler echo-cardiogram. Curve 14 represents an electrocardiogram trace (ECG). The width of the QRS complex in the electrocardiogram trace 14 is exaggerated to facilitate the explanation of the invention. Curve 16 in FIG. 1 is a peripheral pulse waveform, for example a waveform of the pressure pulse taken at the patient's radial artery. In accordance with the invention, the patient's electrocardiogram 14 and radial pressure pulse waveform 16 are measured simultaneously. The horizontal axis at the bottom of FIG. 1 represents time in milliseconds. A typical cycle for a heart beat might take one second or one thousand milliseconds.

Generally speaking, a full cardiac cycle is divided into systole, which corresponds to contraction of the ventricles, and diastole which corresponds to the relaxation of the ventricles. In general terms, systole includes a pre-ejection time (PET) interval, and an ejection duration (ED), which is the amount of time that the aortic valve is open during the cycle. The pre-ejection time (PET) consists of electromechanical delay (EMD) which is typically defined as the time interval from the onset of the Q-wave 14A in the electrocardiogram 14 to the onset of physical cardiac contraction 12A, plus the isovolumetric contraction time (IVCT), which is the initial period of ventricular contraction after the mitral valve closes but before the aortic valve opens. In accordance with one preferred embodiment of the invention, the system detects the minimum value 14B of the Q-wave in the electrocardiogram 14 as an approximation to the onset of the QRS complex. Alternatively, the system can detect the onset of the QRS complex directly or the peak of the R wave. This time is designated as $T_0$ on axis 18 in FIG. 1. As is illustrated by curve 12, there is no blood outflowing from the left ventricle during isovolumetric contraction (IVCT). As the pressure within the left ventricle increases during isovolumetric contraction, the pressure eventually opens the aortic valve and blood flows from the left ventricle into the aorta, as indicated by reference number 12B. The time at which the aortic valve opens and blood begins to flow from the left ventricle, reference number 12B, is designated in FIG. 1 as $T_1$ along the time axis 18. FIG. 1 does not illustrate the pressure waveform in the central aorta, but if such waveform were available, the time $T_1$ would correspond to the foot of the central aortic pulse waveform, and the time interval $T_1 - T_0$ would directly represent the pre-ejection time (PET) interval. However, FIG. 1 illustrates a radial pressure pulse waveform 16, not a central aortic pressure waveform. The foot 16A of the systolic portion of the radial pressure waveform occurs at time $T_2$, which is delayed and later in time than $T_1$, see time axis 18. Nevertheless, as long as the patient's peripheral pressure pulse waveform is measured at a fixed location, such as a fixed location on the patient's wrist, the time interval $T_2 - T_1$ is a constant value (K). In accordance with the invention, therefore, the time interval $T_2 - T_0$ represents the pre-ejection time (PET) plus a constant time value (K), the sum of which is referred to herein as a surrogate pre-ejection time (SPET), i.e., PET+K=SPET. The invention preferably determines the time $T_2$ (i.e. the foot 16A of the peripheral pressure wave) in the manner disclosed in U.S. Pat. No. 5,265,011 to O'Rourke, entitled "Method For Ascertaining The Pressure Pulse And Related Parameters In The Ascending Aorta From The Contour Of The Pressure Pulse In The Peripheral Arteries" issuing on Nov. 23, 1993, which is herein incorporated by reference; namely, by analyzing the first derivative of the peripheral pressure waveform and identifying the first negative to positive zero crossing preceding the maximum value for the first derivative.

The ejection duration (ED) of the left ventricle is completed when the left ventricle begins to relax and the aortic valve closes. Reference number 12C identifies the time ($T_3$) in which the aortic valve closes on curve 12. Referring now again to the peripheral pulse waveform 16, the waveform includes an incisura 16B, which is a high frequency notch in the waveform 16 resulting from the closure of the aortic valve. Time $T_4$ on the time axis 18 corresponds to the realization of the incisura 16B in the peripheral pulse waveform 16. While the form of the peripheral pulse waveform 16 is shifted or delayed in time with respect to the central aortic pressure pulse, and also very likely takes on a somewhat different form, see incorporated U.S. Pat. No. 5,265,011, the time interval from the foot 16A of the peripheral pressure pulse wave to the incisura 16B (i.e., $T_4 - T_2 =$ ED) corresponds accurately to the ejection duration (ED) defining the time interval between the opening 12A of the aortic valve and the closing 12B of the aortic valve. The preferred manner of detecting the location of the incisura 16B in the peripheral pulse wave 16 is disclosed in the above incorporated U.S. Pat. No. 5,265,011; namely, by taking the third derivative of the peripheral pressure waveform and identifying the first positive to negative zero crossing following the largest maximum after a second shoulder in the peripheral pressure waveform unless a second shoulder cannot be identified, in which case the first positive to negative zero crossing following the largest maximum point of the third derivative after the first shoulder.

Figure 2:
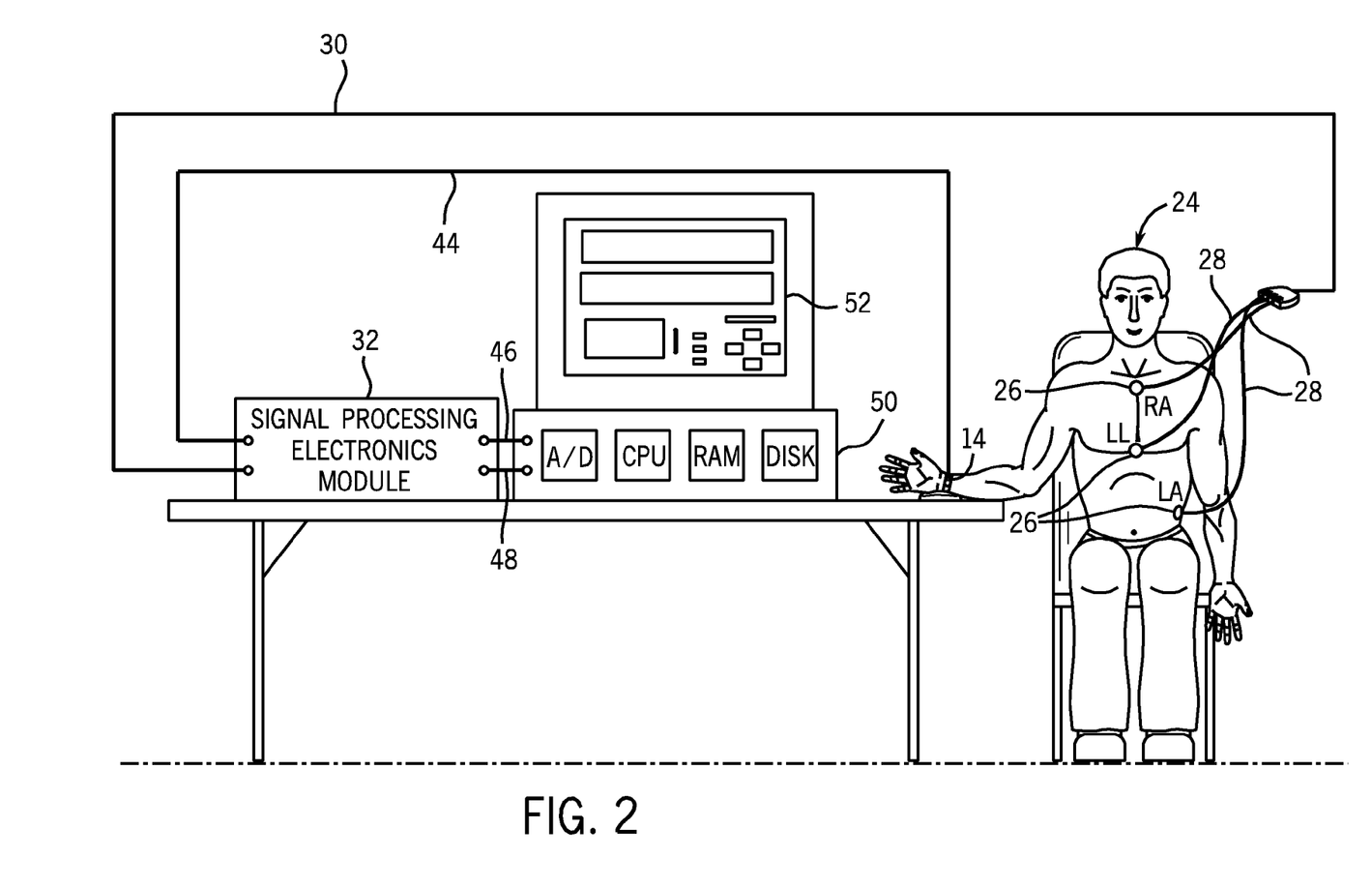
FIG. 2 is a schematic drawing illustrating a system constructed in accordance with the preferred embodiment of the invention.

FIG. 2 is a schematic drawing illustrating the use of the invention. The patient 24 has been prepared to undergo CRT optimization, although the wand and the external CRT programming electronics are not shown for the sake of simplicity. Electrocardiogram electrodes 26 are placed on the patient's chest, as is known in the art. Alternatively, the electrodes can be placed on the peripheral limbs, as also is known in the art. Leads 28 from the electrodes 26 are connected to an ECG cable 30 which in turn is connected to a signal processing electronics module 32. As mentioned, the preferred signal processing electronics module 32 is the SphygmoCor® MM3, manufactured by AtCor Medical. As is known in the art, the electrode leads 28 and cable 30 need to be compatible with the signal processing electronics module 32. A tonometer 34 monitors the patient's radial artery pressure waveform. A conventional hand-held tonometer from AtCor Medical is suitable for carrying out the invention, although it is preferred that the tonometer 34 be strapped to the wrist of the patient 24 in order to ensure that the radial pressure pulse wave be taken at a fixed location on the patient's limb during the CRT optimization session. If desired, the patient's peripheral pressure waveform can be taken at another location, for example, a brachial artery pressure waveform can be measured using an upper arm cuff. In any event, it is important that the location of the peripheral pressure waveform be measured at a fixed location during the CRT optimization session in order to ensure that the pressure pulse travel time from the aortic valve to the peripheral measurement location (e.g., wrist, or upper arm). Since the invention relies on the simultaneous measurement of an electrocardiogram and a peripheral pressure pulse waveform, the accuracy of the invention depends in large part on the measuring of the peripheral pressure waveform at a fixed location.

Figure 5:
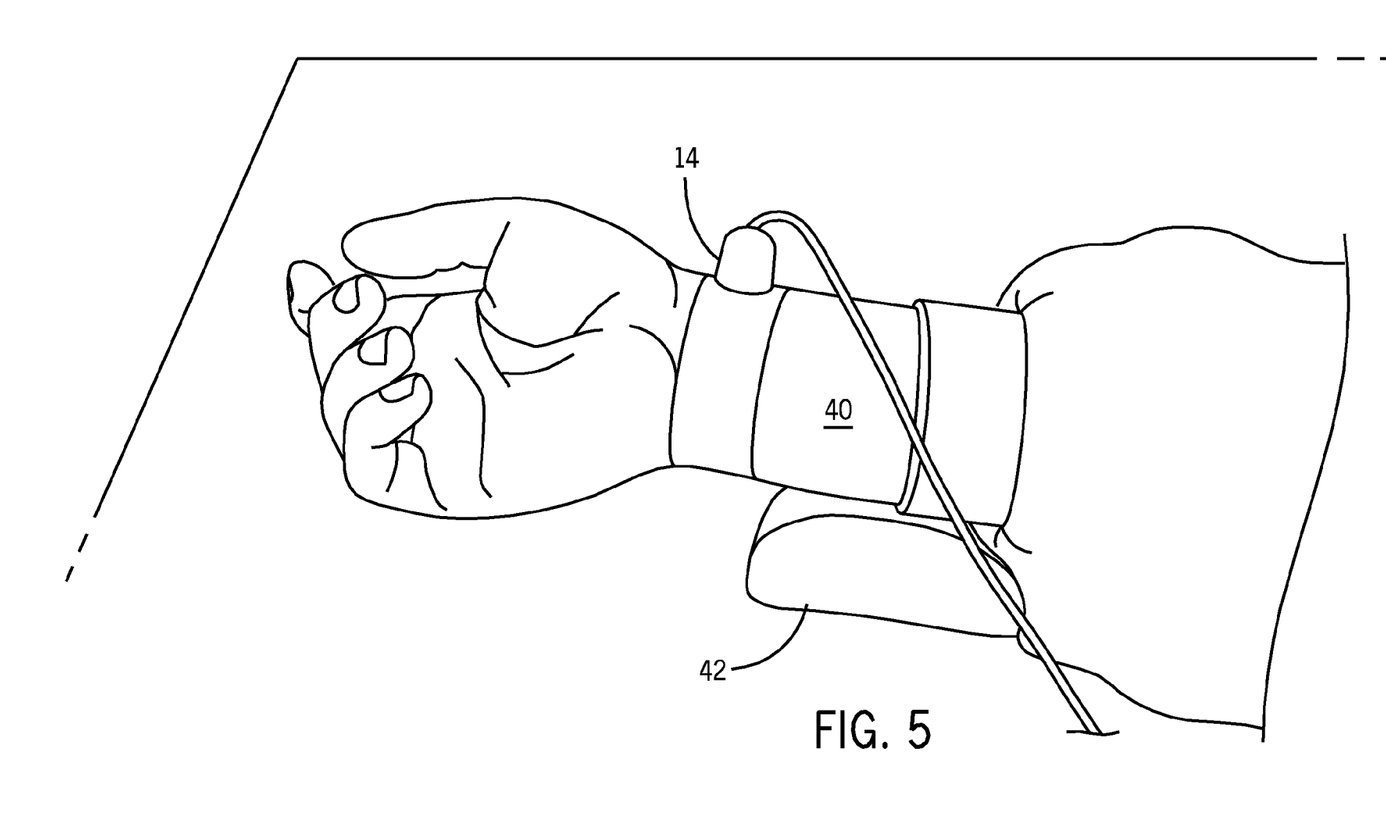
FIG. 5 is a view illustrating the use of a wrist-mounted tonometer as in accordance with the preferred embodiment of the invention.

FIG. 5 illustrates the preferred tonometer device 38 which includes a tonometer sensor or transducer 34 attached to a wrist strap 36. As shown in FIG. 5, the strap 36 is preferably wrapped around the patient's wrist 40 so that the face of the tonometer sensor 34 is placed transcutaneously in a fixed location above the radial artery of the patient. Best results are obtained if the wrist is bent outward in the dorsiflex position, which pushes the radial artery towards the surface, thus making it easier to access. When using the dorsiflex position, the wrist 40 should rest on a small cushion 42, as illustrated in FIG. 5. As is known in the art, the pressure of the tonometer against the patient's wrist may have to be adjusted in order to obtain an adequate waveform for the analysis.

Referring again to FIG. 2, the tonometer 34 is attached to the cable 44 which is connected to the signal processing electronics module 32. Analog output cables 46 and 48 are connected between the signal processing electronics module 32 and the personal computer 50. Electrocardiogram data is transmitted in cable 46 whereas peripheral pressure waveform data is transmitted in cable 48. The computer 50 contains an analog to digital converter which receives the analog data in lines 46 and 48 and converts it to digital form. The computer also includes a processing unit, memory, and data storage, as is common in the art. A computer monitor 52 with a screen display is also provided. The computer 50 is programmed with software that displays a trace of the electrocardiogram and the peripheral blood pressure waveform, and also calculates SPET for each pressure pulse, which is referred to in FIGS. 3 and 4 as the "Q-foot interval", as well as trends.

Figure 3:
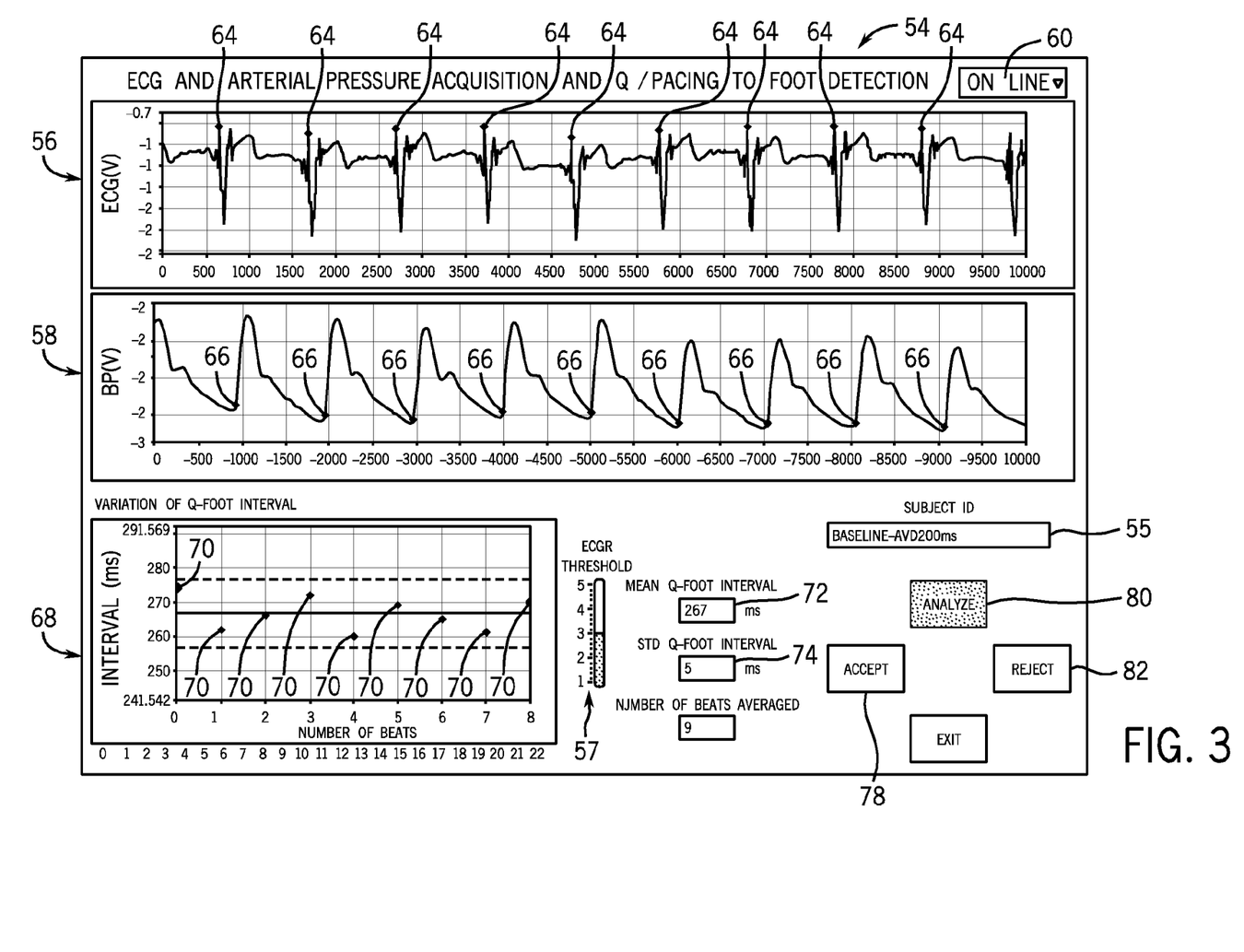
FIG. 3 is a representative screen display on a personal computer in a system implementing a preferred embodiment of the invention.
Figure 4:
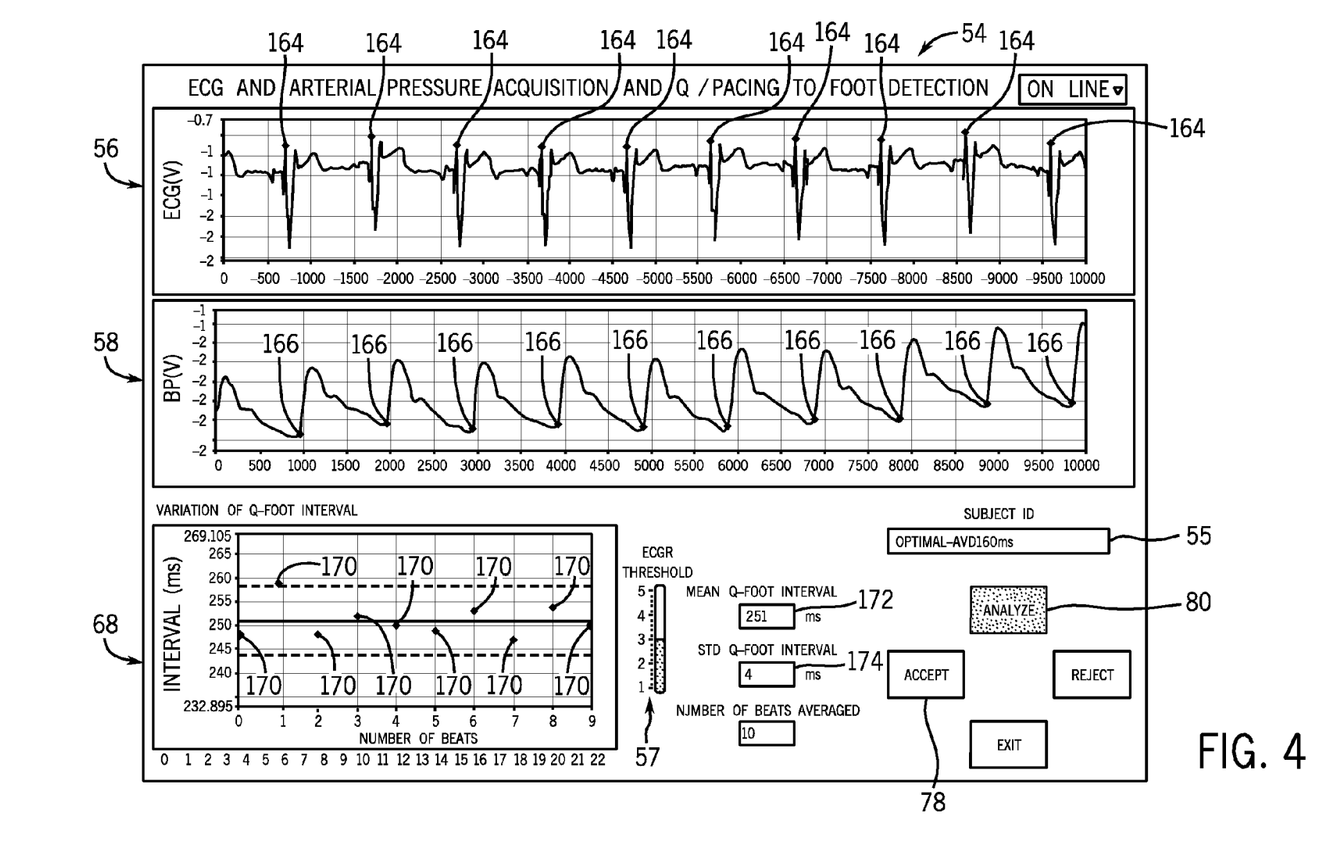

FIGS. 3 and 4 illustrate a computer screen display 54 used to implement the invention. The screen 54 in FIG. 3 contains exemplary data from a patient before CRT optimization. FIG. 4 is similar to FIG. 3, however, the exemplary data is shown for the same patient after CRT optimization. Referring to FIG. 3, patient ID information is entered by the attending staff in box 55 on the screen 54 at the beginning of the session. The screen 54 includes an echocardiogram window 56 and a peripheral blood pressure waveform window 58. The screen 54 also includes an offline/online button 60. When the system is online and collecting data, the electrocardiogram window 56 displays a trace of the electrocardiogram in real-time, and the blood pressure waveform window 58 displays a trace of the peripheral blood pressure waveform, also in real-time. Note that the time scale for the windows 56 and 58 is in milliseconds so the length of the time axis in the windows 56 and 58 corresponds to a ten second interval, which in the case of FIG. 3, corresponds to roughly nine heart beats. After startup, the attending physician or staff observes the quality of the ECG trace and blood pressure waveform trace while the system is online. When the attending staff believes a quality signal has been obtained, the ANALYZE button 80 is selected to stop data acquisition, and the data in windows 56 and 58 remain stationary. FIG. 3 shows the screen at the time at which the ANALYZE button 80 has been selected. At this point, for each respective heart beat, the system in FIG. 3 determines the minimum absolute value of the voltage difference in the Q-wave for the electrocardiogram 56 and defines the corresponding time as the initial impulse time ($T_0$) for the contracting ventricle. In ECG window 56, a dot 64 is illuminated on the electrocardiogram to indicate the time $T_0$ corresponding to the minimum value of the voltage difference of the Q-wave for each heart beat. Note that the y-axis for the electrocardiogram window 56 is progressively negative from the top to the bottom of the chart. Therefore, the minimum value at the Q-wave 64 actually appears towards the top of the chart. The user can set the ECGR threshold 57 in order to set the sensitivity for determining the location for the R-wave. In this embodiment of the invention, the location of the Q-wave is determined by finding the minimum value preceding the R-wave. Of course, other methods can be used to determine the location of the Q-wave and $T_0$. As mentioned, it may be desirable in some cases to detect the onset of the QRS complex directly rather than the minimum value of the Q-wave.

Also for each respective pulse, the system in FIG. 3 determines the realization of systolic onset in the detected peripheral pulse waveform and defines the corresponding time as a peripherally measured systolic onset time ($T_2$). The system places a dot 66 at the foot of the waveform for each pulse.

Screen 54 also includes an interval window 68. The interval window 68 displays the variation of SPET (i.e., $T_2 - T_0 = SPET$), or the "Q-foot Interval", as labeled in FIG. 3, for each heart beat in the ten second trace captured in windows 56 and 58. The "Q-foot interval" (SPET) is illustrated by dots 70 in interval window 68. The system preferably calculates the mean and standard deviation of the calculated SPET values 70 and displays these values on the screen, as indicated by reference numerals 72 and 74. If the attending staff is satisfied with the results of the analysis, the accept button 78 is selected and the data is time-stamped and stored. If the staff is not satisfied that the data is reliable, or for some other reason does not desire to store the information, the reject button 82 is selected.

The system and the information on screen 54 is available for use by the attending physician throughout the process of optimizing the programmable settings for the pacemaker. Button 60 can be selected to take the system offline in order to review past results. FIG. 4 illustrates screen 54, with exemplary data for the same patient as in FIG. 3, but taken after the programmable settings for the pacemaker have been adjusted to optimize cardiac performance. In FIG. 4, reference number 164 depicts the minimum Q-wave value in the electrocardiogram captured after optimization. Reference number 166 represents the foot of the respective peripheral pressure pulses in the blood pressure waveform taken after optimization. In window 68, dots 170 represent the calculated "Q-foot interval" (i.e., SPET) for each of the heart beats for the captured ten second period after optimization. Note that reference number 172 in FIG. 4 indicates that the mean "Q-foot interval" (i.e., mean SPET) after optimization is 251 milliseconds as compared to 267 milliseconds before optimization, see reference numeral 72 shown in FIG. 3. Also, the standard deviation, reference number 174, is slightly lower after optimization in this example than before optimization. The attending physician or staff can select the accept button 78 to store this data with a time-stamp.

With the invention as described, an attending physician and staff are able to minimize pre-ejection time and presumably isovolumetric contraction time using quantitative data that is collected non-invasively and conveniently. In addition, this data is able to be stored for later use in treating the patient. The accessibility of this data facilitates efficient and faster optimization of pacemaker settings. Those skilled in the art will recognize that the invention is not only helpful to facilitate adjustment of settings for biventricular cardiac pacemakers, but also right side only or left side only cardiac pacemakers.

Although not illustrated in FIGS. 3 and 4, the system can also display ejection duration as calculated from the peripheral pressure pulse wave as in the prior art SphygmoCor® system. The system may also calculate and display the ratio SPET/ED and trends of the ratio which staff may find clinically useful.

The foregoing description of the invention is meant to be exemplary. It should be apparent to those skilled in the art that variations and modifications may be made yet implement various aspects or advantages of the invention. It is the object of the following claims to cover all such variations and modifications that come within the true spirit and scope of the invention.

We claim:

1. A method of optimizing one or more programmer settings of a cardiac pacemaker comprising the steps of:
    attending to a patient with a cardiac pacemaker having one or more programmable settings;
    measuring the electrical activity of a heart of the patient in the form of an electrocardiogram which plots a sensed voltage difference between electrodes placed noninvasively on the patient's skin as a function of time, for each pulse of the heart, the electrocardiogram being characterized in part by a Q-wave;
    simultaneously using a sensor to measure a peripheral pressure waveform of the patient as a function of time;
    for each respective pulse, determining from the electrocardiogram a Q-wave and defining a corresponding time as an initial impulse time ($T_0$) for a contracting ventricle;
    for each respective pulse, determining the realization of systolic onset in the detected peripheral pressure waveform and defining the corresponding time as a peripherally measured systolic onset time ($T_2$) for the pulse;
    using $T_0$ and $T_2$ to calculate a surrogate pre-ejection time interval SPET for the pulse;
    presenting information related to the calculated surrogate pre-ejection interval SPET; and
    adjusting one or more of the programmable settings for the cardiac pacemaker in an effort to optimize the value of the calculated surrogate pre-ejection time interval SPET for the patient.

2. A method of optimizing one or more programmer settings of a cardiac pacemaker as recited in claim 1 further comprising the steps of:
    for each respective pulse, determining the time ($T_4$) corresponding to the realization of the closing of the aortic valve in the peripheral pressure waveform;
    using $T_4$ and $T_2$ to calculate an ejection duration time (ED) for the patient;
    presenting information relating to the calculated ejection duration time (ED); and
    further adjusting one or more of the programmer settings for the cardiac pacemaker in an effort to optimize the value of the ejection duration (ED) for the patient.

3. A method of optimizing one or more programmer settings of a cardiac pacemaker as recited in claim 2 wherein the determined time $T_4$ for the closing of the aortic valve in the peripheral pressure wave is determined by taking the third derivative of the peripheral pressure wave and identifying the first positive to negative zero crossing following the largest maximum after a second shoulder in the peripheral pressure wave unless a second shoulder cannot be identified, in which case the first positive to negative zero crossing following the largest maximum point of the third derivative after the first shoulder.

4. A method of optimizing one or more programmer settings of a cardiac pacemaker as recited in claim 2 further comprising the step of: calculating and displaying the ratio SPET/ED.

5. A method of optimizing one or more programmer settings of a cardiac pacemaker as recited in claim 1 wherein the settings are adjusted in an effort to minimize the value of the surrogate pre-ejection time interval SPET.

6. A method of optimizing one or more programmer settings of a cardiac pacemaker as recited in claim 1 wherein the step of determining an initial impulse time ($T_0$) correlating to the Q-wave comprises determining a minimum value of the voltage difference in the Q-wave of the electrocardiogram for each respective pulse.

7. A method of optimizing one or more programmer settings of a cardiac pacemaker as recited in claim 6 wherein the minimum value of the voltage difference in the Q-wave for the electrocardiogram is determined by:
    analyzing the electrocardiogram waveform to:
    identify a largest peak in the electrocardiogram which corresponds to the peak of the R-wave in the electrocardiogram; and
    then identifying a minimum value of the waveform prior to the identified peak in the R-wave of the electrocardiogram.

8. A method of optimizing one or more programmer settings of a cardiac pacemaker as recited in claim 1 wherein the step of determining an impulse time ($T_0$) for a contracting ventricle comprises the step of determining the onset of the QRS complex in the electrocardiogram for the respective pulse.

9. A method of optimizing one or more programmer settings of a cardiac pacemaker as recited in claim 1 wherein the peripheral pressure waveform is a radial artery pressure waveform measured by a tonometer.

10. A method of optimizing one or more programmer settings of a cardiac pacemaker as recited in claim 9 wherein the tonometer is strapped to the wrist of the patient in a fixed location to sense the pressure in the patient's radial artery.

11. A method of optimizing one or more programmer settings of a cardiac pacemaker as recited in claim 1 wherein the peripheral pressure waveform is a brachial pressure waveform measured by a cuff on the patient's upper arm.

12. A method of optimizing one or more programmer settings of a cardiac pacemaker as recited in claim 1 wherein a mean value for the surrogate pre-ejection time interval SPET is calculated as the average difference between the determined initial contraction time $T_0$ and the determined peripheral systolic onset time $T_2$ for a series of pulses and is presented.

13. A method of optimizing one or more programmer settings of a cardiac pacemaker as recited in claim 1 wherein the onset of systole in the measured peripheral pressure waveform is determined by analyzing the first derivative of the peripheral pressure waveform and identifying a first negative to positive zero crossing preceding a maximum value for the first derivative.

14. A method of optimizing one or more programmer settings of a cardiac pacemaker as recited in claim 1 wherein the cardiac pacemaker is a biventricular cardiac pacemaker.

15. A system to facilitate optimization of programmable cardiac pacemaker settings during cardiac resynchronization therapy, the system comprising:
 a blood pressure sensor adapted to detect a peripheral pressure waveform of a cardiac pacemaker patient;
 an electrocardiogram unit having electrodes that are placed on the patient, the ECG unit measuring the electrical activity of the patient's heart in the form of an electrocardiogram which is, for each pulse of the heart, characterized in part by a Q-wave;
 a screen display; and
 a computer processor programmed with software to implement the following steps:
  for each respective pulse, determining from the electrocardiogram Q-wave and defining the corresponding time as an initial impulse time ($T_0$) for a contracting ventricle;
  for each respective pulse, determining systolic onset of the detected peripheral pressure wave and defining the corresponding time as a peripherally measured systolic onset time ($T_2$) for the pulse; and
  using ($T_0$) and ($T_2$) to calculate a surrogate pre-ejection time interval SPET; and
  displaying information on the screen relating to the calculated surrogate pre-ejection time interval SPET.

16. A system as recited in claim 15 wherein the blood pressure sensor is a tonometer.

17. A system as recited in claim 16 wherein the tonometer is mounted to a strap adapted to hold the tonometer against the wrist of a patient in a fixed location to monitor the patient's radial artery.

18. A system as recited in claim 17 wherein the software provides a graphical representation on the screen display of the patient electrocardiogram data and the patient peripheral blood pressure waveform data, both as a function of time.

19. A system as recited in claim 15 wherein the computer processor is contained within a personal computer onto which the software is loaded; and the system further comprises a digital signal processing electronic module which is electrically connected to the blood pressure sensor and to leads for the ECG electrodes, and provides analog data for the electrocardiogram and the peripheral pressure waveform that is transmitted to an analog to digital converter which provides digital data in real-time to the personal computer.

20. A system as recited in claim 19 wherein the personal computer is capable of storing patient electrocardiogram and peripheral pressure waveform data for later analysis.

21. A system as recited in claim 15 wherein the software further analyzes ECG data and peripheral pressure waveform data collected over a fixed time period and calculates averages of the SPET for the heart beats within the fixed time period as well as a standard deviation of SPET for the heart beats in the fixed time period.

22. A system as recited in claim 15 wherein the computer is programmed to determine systolic onset of the detected peripheral pressure waveform by analyzing a first derivative of the peripheral pressure waveform and identifying a first negative to positive zero crossing preceding a maximum value for the first derivative.

\* \* \* \* \*